United States Patent [19]

Cameron et al.

[11] Patent Number: 5,523,493
[45] Date of Patent: Jun. 4, 1996

[54] PROCESS FOR THE PRODUCTION OF AT LEAST ONE ALKYL TERTIOBUTYL ETHER FROM NATURAL GAS

[75] Inventors: Charles Cameron, Paris; Patrick Chaumette, Bougival; Quang Dang Vu, Neuilly Sur Seine; Jacques Bousquet, Irigny; Jacquos Tournier-Lasserve, Pau; Guy Desgrandchamps, Billere, all of France

[73] Assignees: Institut Francais Du Petrole, Rueil Malmaison; Elf Aquitaine Production, Courbevoie, both of France

[21] Appl. No.: 324,145

[22] Filed: Oct. 17, 1994

[30] Foreign Application Priority Data

Oct. 15, 1993 [FR] France ................... 93 12404

[51] Int. Cl.⁶ ................................................. C07C 41/00
[52] U.S. Cl. .................................................. 568/671
[58] Field of Search ..................................... 568/671

[56] References Cited

U.S. PATENT DOCUMENTS 4,731,490  3/1988  Coughenour et al. ............... 568/697

FOREIGN PATENT DOCUMENTS 0336823  10/1989  European Pat. Off. .
2080297  2/1982   United Kingdom .
2123411  2/1984   United Kingdom .
2227249  7/1990   United Kingdom .

OTHER PUBLICATIONS

J. Foreman, "Adding Another Step to Steam Reforming Aves Fuel and Boosts Output," *Hydrocarbon Processing*, vol. 69, No. 12, Dec. 1990, pp. 34B–34D.

*Primary Examiner*—Paul J. Killos
*Attorney, Agent, or Firm*—Millen, White, Zelano, & Branigan

[57] ABSTRACT

The invention concerns a process for the synthesis of at least one alkyl tertiobutyl ether, preferably respectively MTBE or ETBE, from at least one alcohol and from isobutene, each synthesized at least partially from natural gas. The alcohol, preferably methanol or ethanol respectively, is synthesized at least partially from synthesis gas, a portion of said synthesis gas being prepared in natural gas steam prereforming zone. The isobutene is synthesized in a series of processes which includes direct transformation of natural gas to ethylene, known as oxidative coupling of methane (OCM), dimerization of ethylene to normal butene, isomerization of n-butene to isobutene, and the separation units associated therewith.

10 Claims, 1 Drawing Sheet

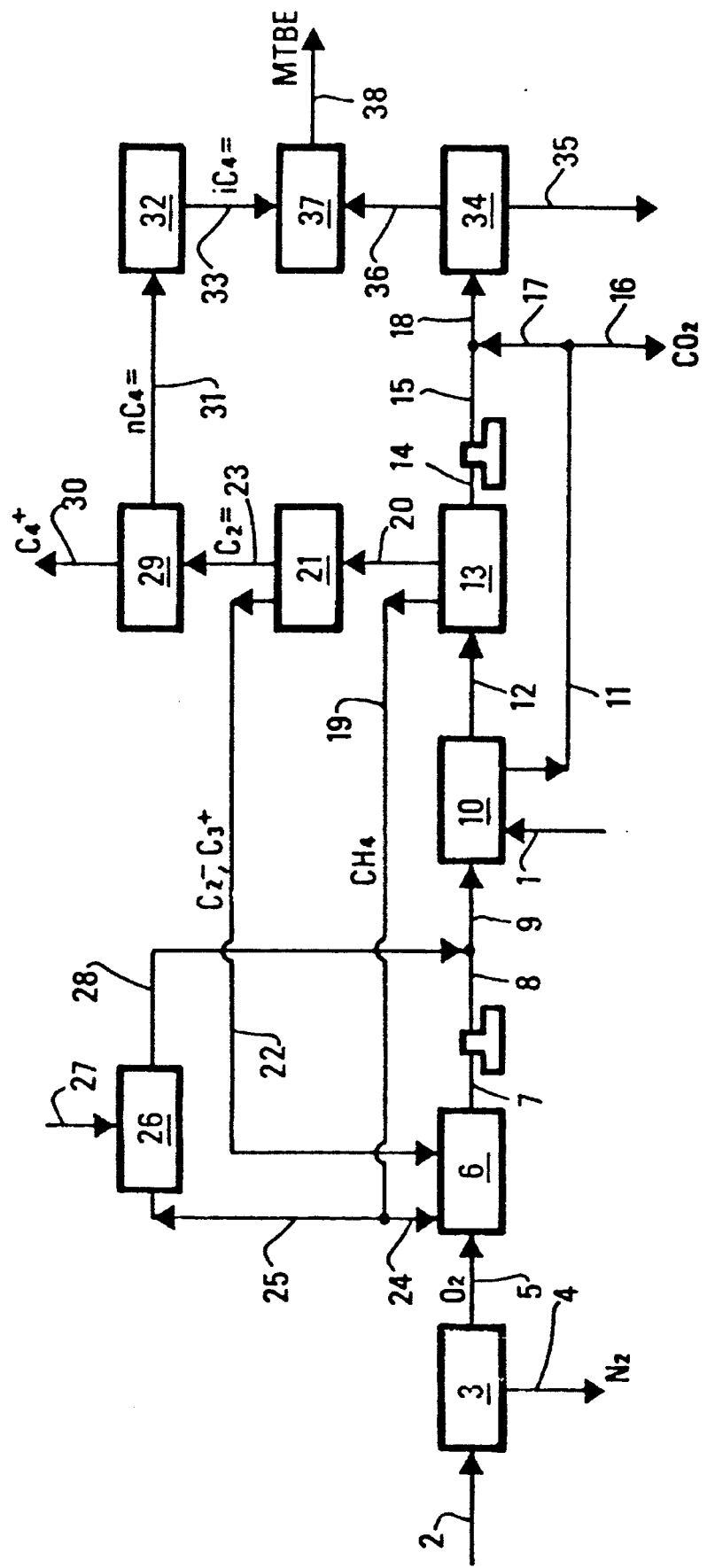

PROCESS FOR THE PRODUCTION OF AT LEAST ONE ALKYL TERTIOBUTYL ETHER FROM NATURAL GAS

BACKGROUND OF THE INVENTION

The present invention concerns a process for the production of at least one alkyl tertiobutyl ether at least partially from natural gas.

Natural gas is an abundant raw fossil material mainly constituted by methane, whose current known reserves, of the order of $10^{14}$ m$^3$, represent about 50 years of world consumption. The gas fields frequently contain large quantities of ethane, propane, other high alkanes ($C_3^+$ hydrocarbons, i.e., hydrocarbons containing at least 3 carbon atoms per molecule), as well as other constituents such as $H_2O$, $CO_2$, $N_2$, $H_2S$ and He. The majority of the propane and other high alkanes associated with natural gas are liquefied as LPG (liquid petroleum gas). In helium rich fields (generally more than 0.3% by volume), helium is separated out because of its high commercial value. Hydrogen sulphide is also separated out because of its corrosive nature, and also water to prevent the formation of hydrates which make the transport of natural gas difficult. Natural gas can be purified by dehydration and desulphurisation, preferably to a sulphur compound content of less than 10 ppm. It is then termed uncondensed gas and contains mainly methane (for example, 55–99% by volume), also ethane, usually propane and may contain small amounts of nitrogen and/or carbon dioxide.

However, the term natural gas is indiscriminately applied to purified gas obtained by dehydration and desulphurisation, and to unpurified gas obtained directly from a field and not subjected to any purification whatsoever.

Most natural gas is used for private and industrial heating. However, some processes exist for transforming natural gas into higher hydrocarbons.

Transformation of natural gas into alkyl tertiobutyl ether(s), such as methyl tertiobutyl ether (MTBE) or ethyl tertiobutyl ether (ETBE) respectively, is highly desirable. Alkyl tertiobutyl ethers are currently produced by reacting isobutene with an alcohol, such as methanol or ethanol respectively, and while said alcohols are readily synthesized from natural gas via synthesis gas (defined as a mixture containing carbon monoxide, hydrogen and, optionally, carbon dioxide), this is not the case for isobutene which is normally extracted from a $C_4$ (hydrocarbons containing 4 carbon atoms per molecule) cut, produced from a catalytic cracking unit for petroleum cuts, for example. This source of olefins is now far too limited to fulfil the increasing demand for alkyl tertiobutyl ether(s) such as MTBE or ETBE. For this reason, a method of producing alkyl tertiobutyl ethers from natural gas would be of interest.

SUMMARY OF THE INVENTION

An object of the invention is to synthesize at least one alkyl tertiobutyl ether, preferably respectively MTBE or ETBE, from at least one alcohol and from isobutene, each synthesized at least partially from natural gas. In the process of the invention, the alcohol, preferably respectively methanol or ethanol, is synthesized from synthesis gas, said synthesis gas being itself partially prepared in a natural gas steam prereforming zone. The isobutene is synthesized in a series of processes which includes direct transformation of natural gas to ethylene, known as oxidative coupling of methane (OCM), dimerisation of ethylene to normal butene, isomerisation of n-butene to isobutene, and the separation units associated therewith. The process for the production of at least one alkyl tertiobutyl ether from natural gas is termed the oxyetherification process.

United States patent U.S. Pat. No. 5,159,125 claims a process for aldol condensation of methanol or other alcohols with an olefin containing at least two carbon atoms, to synthesize an isobutanol-rich mixture of higher molecular weight alcohols. The isobutanol can then be separated and dehydrated to form isobutene and said isobutene is condensed with methanol to form MTBE. These processes are known to the skilled person.

A further object of the process of the invention is to utilise the by-products of non selective oxidation of natural gas in the OCM reactor, i.e., carbon monoxide and carbon dioxide, as well as the hydrogen which is produced at the same time, as synthesis gas which at least partially supplies the unit for synthesizing at least one alcohol.

Ethylene and other hydrocarbons can be produced by oxidative coupling of methane or a cut containing mainly methane in either sequential or simultaneous mode.

Sequential mode oxidative coupling reaction consists in oxidising methane with a reducible agent followed by separate reoxidation of said agent by the oxygen in air. A number of metal oxides, in particular Mn, Ce, Pr, Sn, In, Ge, Pb, Sb, Bi, and Tb have been cited for use as reducible agents for this reaction in a number of United States patents, for example U.S. Pat. Nos. 4,499,323, 4,523,049, 4,547,611 and 4,567,307.

The simultaneous mode oxidative coupling reaction (passing a mixture of methane and oxygen over a contact mass) can be written qualitatively as follows:

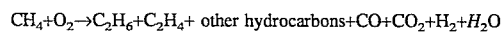

$$CH_4 + O_2 \rightarrow C_2H_6 + C_2H_4 + \text{other hydrocarbons} + CO + CO_2 + H_2 + H_2O$$

A number of patent documents (for example European patent applications EP-A2-210 383, EP-A1-189 079, EP-A1-206 044 and PCT application WO 86 07351) mention the use of rare earth oxides, alkali and alkaline-earth oxides and titanium, zirconium, hafnium and zinc oxides either alone or mixed together as catalysts for oxidative coupling reaction of methane in simultaneous mode.

Because of the occasionally appreciable presence of propane and sometimes of other high alkanes in natural gas, and occasionally the presence of light hydrocarbons from other units located, for example, close to the natural gas oxidative coupling unit, it is very advantageous to utilise propane and occasionally other high alkanes as well as methane and ethane.

U.S. Pat. No. 5,025,108 thus claims a process for the oxypyrolysis of natural gas in which the natural gas is separated into two fractions, a first methane-rich fraction which is selectively oxidised by molecular oxygen in the presence of a contact mass (oxidative coupling of methane, OCM) to form an effluent which contains $C_2$ hydrocarbons and water as the principal products, the effluent also containing small quantities of CO, $CO_2$ and $H_2$, and a second fraction of $C_2^+$ hydrocarbon enriched gas (i.e. containing at least 2 carbon atoms per molecule) which is mixed with said effluent when at least about 80% by volume of the molecular oxygen has been consumed in the methane oxidation step, the resulting mixture then being pyrolysed.

A further possibility (U.S. Pat. No. 5,113,032) consists of separating the natural gas into three fractions in an oxypyrolysis process, i.e., a first methane-rich fraction, a second $C_2$-rich fraction and a third $C_3^+$ hydrocarbon-rich fraction, and to separately pyrolyse said second and third fractions to increase the ethylene yield, or to pyrolyse said second fraction and independently utilise the $C_3^+$ cut using any other process which is known to the skilled person.

The present invention thus also concerns a process for the production of at least one alkyl tertiobutyl ether at least partially from natural gas wherein the ethylene required for isobutene production is produced by the oxypyrolysis process claimed in United States patents U.S. Pat. Nos. 5,025,108 and 5,113,032.

Some of the advantages of the oxyetherification process for natural gas of the present invention are:

a) the synthesis of at least one alkyl tertiobutyl ether is carried out using isobutene and alcohol(s) which are at least partially prepared from natural gas;

b) the preparation of the synthesis gas necessary for the synthesis of at least one alcohol does not necessitate the installation of an expensive steam reforming unit for methane or a partial oxidation unit. A simple prereforming unit can produce most of the synthesis gas, the remainder being supplied by the OCM unit;

c) the use of carbon oxides (CO, $CO_2$) and hydrogen from the OCM reaction as synthesis gas for the production of at least one alcohol means that the by-products of this reaction can be better utilised.

The oxyetherification process of the invention, for synthesizing at least one alkyl tertiobutyl ether, preferably respectively methyl tertiobutyl ether or ethyl tertiobutyl ether, at least partially from natural gas, preferably purified, comprises the following steps:

(a) Steam prereforming a feedstock containing mainly natural gas, preferably practically free of $CO_2$, and more preferably purified, in a prereforming zone in the presence of a contact mass to partially convert this fraction to an effluent containing mainly hydrogen and carbon oxides (CO, $CO_2$). Said feedstock is preferably methane-rich and generally contains methane, ethane, propane, other hydrocarbons which are associated with natural gas and, possibly, non hydrocarbon gases. Prior to prereforming, said feedstock may be separated into a first fraction containing mainly methane, preferably substantially free of ethane, propane and other hydrocarbons which are associated with natural gas, said fraction then constituting the actual feedstock for the prereforming zone, and into a second fraction containing mainly hydrocarbons containing at least two carbon atoms per molecule (in particular mainly ethane and propane, and may or may not also contain non hydrocarbon gases), which can either be utilised in the process, for example by mixing it with the fifth fraction described in step (c) below and injecting said mixture into the section of the oxypyrolysis zone in which pyrolysis is effected, or purged. This optional prior separation step can be carried out in a specific fractionation zone. However, it is preferably carried out in the separation zone described in step (c) below in order to minimise investment costs.

The prereforming process has been described, for example, by British Gas (Hydrocarbon Processing, p34, December 1990). All the $C_2^+$ hydrocarbons present in the feedstock are decomposed to methane. This latter establishes reforming equilibrium with hydrogen, carbon oxides and water vapour.

(b) A major portion of the effluent from prereforming step (a) is mixed with a major portion of the second effluent from the OCM zone described in step (d) below, which has been dried and compressed.

(c) The mixture formed in step (b) is then sent to a separation zone to produce the following effluents:
a first fraction containing mainly carbon dioxide,
a second fraction containing mainly methane,
a third fraction containing mainly ethylene,
a fourth fraction containing mainly hydrogen and carbon monoxide,
a fifth fraction containing mainly ethane and $C_3^+$ hydrocarbons.

(d) Oxidative coupling of methane (OCM) is carried out in an OCM zone. When the natural gas is to be oxypyrolysed, the oxypyrolysis zone comprises two successive sections: one section of the oxypyrolysis zone where OCM is effected and a further section of the oxypyrolysis zone where pyrolysis is effected; thus said OCM zone is in fact the section of the oxypyrolysis zone in which OCM occurs. The OCM zone is supplied with at least one gas fraction, preferably enriched in methane, preferably by at least a portion of the second fraction described in step (c). The OCM zone provides a first effluent containing mainly reaction product, i.e., ethylene, and a second effluent containing mainly by-products of the OCM reaction, i.e., hydrogen, carbon monoxide and carbon dioxide.

When an oxypyrolysis zone is present, the supply for the section of the oxypyrolysis zone where pyrolysis is effected is preferably constituted by a major portion of the fifth fraction described in step (c) as described in United States patent U.S. Pat. No. 5,025,108 cited above. More preferably, said fifth fraction is separated into a first stream containing mainly ethane and a second stream containing mainly $C_3^+$ hydrocarbons, either to supply the section of the oxypyrolysis zone where pyrolysis is effected with at least a portion of said two streams which will be separately pyrolysed, as described in United States patent U.S. Pat. No. 5,113,032 cited above, or to supply the section of the oxypyrolysis zone where pyrolysis is effected with a major portion of said first stream and a major portion of said second stream is purged.

(e) A major portion of the first effluent obtained in step (d), to which a major portion of the third fraction described in step (c) has preferably been added, is dimerised in a dimerisation zone to produce an effluent containing mainly n-butene.

(f) A major portion of the effluent obtained in step (e) is isomerised in an isomerisation zone to produce an effluent containing mainly isobutene.

(g) Synthesis of at least one alcohol, preferably respectively methanol or ethanol, is carried out in an alcohol synthesis zone, from a portion, preferably a major portion, of the fourth fraction obtained from step (c) and a portion, preferably a major portion, of the first fraction obtained from step (c) and optionally a portion, preferably a major portion, of the second effluent obtained in step (d), said portions of the fractions or optionally the second effluent being compressed and preferably completely mixed together before introduction into the alcohol synthesis zone to form at least a portion of the synthesis gas required for alcohol manufacture in the alcohol synthesis zone. A further portion of the synthesis gas required for the alcohol manufacture may optionally be introduced to the entrance to the alcohol synthesis zone from a further onsite or even offsite unit.

In the particular case of methanol synthesis, which may be an industrial synthesis, a feature of the process of the present invention is that all the streams supplying the alcohol synthesis zone are combined so that the gas supplying said zone has a $H_2/(2CO+3CO_2)$ ratio generally equal to about 1, i.e., generally between 0.8 and 1.2, preferably between 0.9 and 1.1.

In the particular case of ethanol synthesis, two steps can be used: methanol is synthesized in a first step then, in a second step, a major portion of the methanol synthesized in the first step is transformed into ethanol, for example by homologation. A further portion of the ethanol may also be synthesized by hydration of ethylene.

The alcohol synthesis zone can also be an onsite zone which is partially used for step (g) of the process of the invention.

Finally, an effluent is obtained from the alcohol synthesis zone which mainly contains at least one alcohol, preferably methanol or ethanol respectively.

(h) A major portion of the effluent obtained from step (f) is combined with at least a part, preferably a major part, of the effluent obtained from step (g) which is optionally completed by importing a further effluent mainly containing at least one alcohol supplied from a further onsite or an offsite unit, to synthesize at least one alkyl tertiobutyl ether, preferably respectively MTBE or ETBE, in an alkyl tertiobutyl ether synthesis zone.

Regarding the contact mass in the prereforming zone (step (a) in the process of the invention), any contact mass which is known for this application can be used, for example a contact mass based on nickel dispersed on an oxide and preferably with a large specific surface area such as an alumina or stabilised alumina.

Regarding the contact mass used in the oxidative coupling of methane zone, i.e., selective oxidation of methane to higher hydrocarbons (step (d) of the process of the invention), it is preferable to use a contact mass which satisfies the three following conditions:

1) it must be capable of operating under normal oxidative coupling conditions, for example at a temperature generally between 650° C. and 1200° C., preferably between 650° C. and 950° C., 2) it must produce $C_2^+$ hydrocarbons with a selectivity of generally at least 65% for conversion of 15% methane, and 3) it must maintain its activity and selectivity over many hours of operation.

Contact masses which satisfy the above conditions and which are thus preferred for use in the process of the invention are generally those which contain oxides and/or carbonates of alkali metals (such as lithium, sodium, potassium, rubidium and caesium), alkaline-earth metals (such as berylium, magnesium, calcium, strontium and barium) and rare earth metals (such as yttrium, lanthanum, praseodymium, neodymium, samarium, gadolinium, terbium, dysprosium, holmium, erbium, thulium, ytterbium, europium and lutecium), either alone (as in the case of rare earths and alkaline-earths) or as a mixture (as in the case of alkaline-earth metals doped with alkali metals and rare earth metals doped with alkali and/or alkaline-earth metals). Other contact masses which satisfy the above conditions are those which contain oxides and/or carbonates of titanium, zirconium, hafnium, manganese, cerium, tin, indium, germanium, lead, antimony, zinc and bismuth, preferably with one or more oxides and/or carbonates of alkali, alkaline-earth or rare earth metals and silica. The contact masses described above are effective on their own or doped with halides, phosphorous oxides or sulphur. The contact masses are not, however, limited to the formulae indicated above: more generally, any contact mass which is suitable for this application may be used.

The gas fraction, which is preferably methane enriched and oxidised (step (d) of the process of the invention) can be used without a diluant or can be diluted with at least one inert gas such as nitrogen, carbon dioxide or steam. For safety reasons and to avoid too great an increase in temperature, which would adversely affect the selectivity of the operation, the oxygen content in the methane should not in general exceed 40 mole %; it is thus generally between 0.1 and 40 mole %, preferably between 5 and 25 mole %.

The temperature of the oxidative coupling reaction (OCM) (step (d) of the process of the invention) is generally between 650° C. and 1200° C., preferably between 650° C. and 950° C.

The total pressure in the OCM zone (step (d) of the process of the invention) is generally between 1 and 100 bar (1 bar=$10^5$ Pa), preferably between 1 and 20 bar. The contact time (i.e., the time required to consume at least 80% of the molecular oxygen in the feedstock) is normally between $10^{-6}$ and 1 second, preferably between $10^{-6}$ and $10^{-1}$ second.

The OCM reaction may be carried out in any type of reactor, in particular in a fixed bed, mobile bed, circulating bed or fluidised bed reactor, preferably a fixed bed reactor.

Regarding the contact mass used for the ethylene dimerisation reaction (step (e) in the process of the invention), any contact mass or any soluble catalyst which is known for this application may be used, such as a nickel salt deposited on an oxide support such as alumina or, for example, a mixture of soluble nickel-containing complexes and a Lewis acid such as a mixture of a nickel carboxylate and a trialkylaluminium. A mixture of an alkyl titanate and an alkyl hydrocarbyl aluminium may also be used to selectively dimerise ethylene to but-1-ene as indicated in United States patents U.S. Pat. Nos. 4,532,370, 4,615,998 and 4,721,762.

Regarding the contact mass used for the isomerisation of n-butene to isobutene (step (f) of the process of the invention), any contact mass which is known for this application can be used, in particular any contact mass with a very low acidity such as aluminas, which may be doped, silica-aluminas, silica-zirconias, or zeolites. It is particularly possible and advantageous to use the contact masses described in French patent application FR-A-2.695.636.

Synthesis of at least one alcohol (step (g) of the process of the invention) is carried out using any process which is known to the skilled person. Thus, methanol synthesis from synthesis gas is an industrial process which is generally carried out in the presence of copper based catalysts and has been described in, for example, United States patents U.S. Pat. Nos. 3,388,972 and 3,546,140 from CCI and U.S. Pat. No. 3,923,694 from ICI. Any contact mass which is known for this application can be used, such as copper, aluminium and zinc based catalysts described in United States patent U.S. Pat. No. 5,112,591. Synthesis of mixtures of alcohols have been described by us, for example in United States patents U.S. Pat. Nos. 4,780,481 and 4,791,141. Any contact mass which is known for this application may be used in this process. Catalysts based on group VIII metals such as nickel, iron and molybdenum have been described in the literature, and copper and cobalt based catalysts as described in United States patent U.S. Pat. No. 4,791,141 may be used.

Regarding the contact mass used for the reaction synthesizing at least one alkyl tertiobutyl ether (step (h) of the process of the invention), any contact mass which is known for this application may be used, for example acid resins such as sulphonic resins or any acidic oxide or zeolite with an adequate acidity. This synthesis is described, for example, in United States patents U.S. Pat. Nos. 4,847,431, 5,013,407 and 4,847,430.

The process of the invention can also be used to simultaneously prepare at least one alkyl tertiobutyl ether as well as a liquid fuel (for example petrol and/or gas oil) by dimerisation and/or oligomerisation of a portion of the olefins produced during oxidative coupling of methane (step (d) of the process of the invention), as has been described, for example, in United States patents U.S. Pat. Nos. 5,025,108 and 5,113,032. In this case, prereforming step (a) of the process of the invention can be deleted and only synthesis gas from step (d) (i.e., the second effluent from the OCM zone) is then used for alcohol production. The alcohol(s) is (are) advantageously then transformed into alkyl tertiobutyl ether(s) by reaction, in step (h) of the process of the invention, with the isobutene produced by dimerisation and isomerisation (steps (e) and (f) of the process of the invention) of the remaining ethylene fraction which has not been transformed into liquid fuel. The process of the invention can thus be used to produce a high performance liquid fuel base such as a high octane petrol, by mixing the fuel produced with at least a portion of the alkyl tertiobutyl ether(s) simultaneously produced.

Finally, the invention also concerns a process for the simultaneous production of at least one alkyl tertiobutyl ether and a liquid fuel from natural gas, said process comprising the following steps:

(1) a major portion of the second effluent from the OCM zone described in step (2) is dried and compressed then sent to a separation zone to produce the following effluents:
 a first fraction containing mainly carbon dioxide,
 a second fraction containing mainly methane,
 a third fraction containing mainly ethylene,
 a fourth fraction containing mainly hydrogen and carbon monoxide,
 a fifth fraction containing mainly ethane and $C_3^+$ hydrocarbons, (2) oxidative coupling of methane is carried out in an OCM zone to produce a first effluent containing mainly ethylene and a second effluent containing mainly hydrogen, carbon monoxide and carbon dioxide, (3) a portion of the first effluent obtained from step (2) is dimerised in a dimerisation zone to produce an effluent containing mainly n-butene, (4) a major portion of the effluent obtained from step (3) is isomerised in an isolmerisation zone to produce an effluent containing mainly isobutene, (5) synthesis of at least one alcohol is carried out in an alcohol synthesis zone, using a portion of the fourth fraction obtained from step (1) and a portion of the first fraction obtained from step (1), said portions being compressed before introduction into the alcohol synthesis zone to form an effluent containing mainly at least one alcohol, (6) a further portion of the first effluent obtained from step (2) undergoes at least one of the following reactions: dimerisation or oligomerisation in a reaction zone, to produce an effluent containing mainly liquid fuel, (7) a major portion of the effluent obtained from step (4) is combined with at least a portion of the effluent obtained from step (5) to synthesize at least one alkyl tertiobutyl ether in an alkyl tertiobutyl ether synthesis zone, (8) a major portion of the effluent obtained from step (6) is mixed with a portion of the alkyl tertiobutyl ether(s) to produce a liquid fuel base.

BRIEF DESCRIPTION OF THE DRAWING

The attached drawing is a schematic flowsheet of an embodiment of the invention.

DETAILED DESCRIPTION OF THE DRAWING

The following non limiting example represents an embodiment of the process of the invention which is illustrated in the Figure and can be used to carry out oxyetherification of natural gas in accordance with the invention.
EXAMPLE (in accordance with the invention)

In order to produce 100 000 T/year of MTBE, 860 kmoles/h of natural gas with the following composition (in mole %) were used:

| | |
|---|---|
| $CH_4$ | 88.7 |
| $C_2$ | 5.6 |
| $C_3^+$ | 2.6 |
| $CO_2$ | 2.3 |
| $H_2S$ | 0.8 |
| | 100.00 |

After purification and recovery of the LPG, 810 kmoles/h of a gas containing almost exclusively hydrocarbons containing one or two carbon atoms per molecule was sent via conduit (1) and decarbonated in unit (10).

The product arriving via conduit (12) from unit (10) was separated into three fractions in unit (13), the "cold box".

The first fraction, evacuated via conduit (14) then conduit (15) following compression, was constituted by hydrogen, carbon monoxide and any incondensables present. This fraction served as the supply gas for methanol synthesis unit (34). The composition of this fraction did not correspond to the methanol synthesis stoichiometry. Thus enough $CO_2$ was drawn from the purge from decarbonation unit (10) and sent via conduit (11) and conduit (17) so that adding the gas in conduits (15) and (17) produced a gas supply via conduit (18) for unit (34) which had a $H_2/(2CO+3CO_2)$ ratio of approximately 1. The remaining purged gas from unit (10) which was not taken by conduit (17) was evacuated via conduit (16). Thus, of the 187.5 kmoles/h of purge from unit (10) via conduit (11), 107.5 went via conduit (17) and 80 kmoles/h was purged to the atmosphere via conduit (16).

The second fraction containing mainly methane left unit (13) via conduit (19) and a portion (5254 kmoles/h) was sent via conduit (24) to oxidative coupling unit (6) for oxypyrolysis. The other portion of said second fraction (764.5 kmoles/h) was sent via conduit (25) to prereforming unit (26) to produce the hydrogen required for methanol synthesis stoichiometry.

The third fraction, corresponding to 484.5 kmoles/h of $C_2^+$, was sent to fractionation unit (21) via conduit (20).

In unit (26), 764.5 kmoles/h of gas were transformed into 1038.5 kmoles/h of gas (dry state) by virtue of an injection of steam via conduit (27) to form a gas with the following composition:

| | |
|---|---|
| CO | 0.51 |
| $CO_2$ | 6.12 |
| $H_2$ | 25.86 |
| $C_1$ | 67.51 |
| | 100.00 |

Gas arriving from conduit (28) was mixed with the effluent gas from unit (6) in conduit (7) then conduit (8)

following compression, and the mixture in conduit (9) was decarbonated in unit (10).

Decarbonation was necessary to prevent formation of compressed solid $CO_2$ in cold box (13).

Unit (21) firstly separated out $C_3^+$ compounds which were returned via conduit (22) to the pyrolysis section of unit (6) installed downstream of the OCM reactor. The remaining fraction from conduit (20) was then distilled to give 296.5 kmoles/h of ethylene and 172 kmoles/h of ethane. The ethane was also sent to unit (6) via conduit (22) for pyrolysis to ethylene as described in United States patent U.S. Pat. No. 5,025,108. Unit (6) was supplied via conduit (5) with oxygen from air distillation unit (3) which was supplied with air via conduit (2) and producing nitrogen via conduit (4). Finally, the 296.5 kmoles/h of ethylene from unit (21) was sent to dimerisation unit (29) via conduit (23). 142 kmoles/h of n-butene was thus produced at the same time as 620 kmoles/h of a heavy fraction $C_4^+$ which was purged via conduit (30).

The linear butene was sent via conduit (31) to unit (32) which was an isomerisation unit for transforming n-butene into isobutene. The isobutene was sent via conduit (33) to methyl tertiobutyl ether (MTBE) synthesis unit (37) which also received methanol from methanol synthesis unit (34) via conduit (36).

Finally, 12487 kmoles/h of ether, i.e., 100 000 T/year, was obtained from conduit (38). The purge was evacuated via conduit (35). In the present case, all the methanol required for the manufacture of the MTBE, namely 4650 kg/year, had been manufactured from the effluent gas from oxypyrolysis unit (6).

The entire disclosures of all applications, patents, and publications cited above and below and of corresponding French Application 93/12,404, filed Oct. 15, 1993, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for the production of at least one alkyl tertiobutyl ether at least partially from natural gas, said process comprising the following steps:

(a) steam prereforming a feedstock containing mainly natural gas in a prereforming zone in the presence of a contact mass to produce an effluent containing mainly hydrogen, carbon monoxide and carbon dioxide, (b) mixing a major portion of the effluent from prereforming step (a) with a major portion of the second effluent from the OCM zone described in step (d) below, which has been dried and compressed, (c) sending the mixture formed in step (b) to a separation zone to produce the following effluents:
    a first fraction containing mainly carbon dioxide,
    a second fraction containing mainly methane,
    a third fraction containing mainly ethylene,
    a fourth fraction containing mainly hydrogen and carbon monoxide,
    a fifth fraction containing mainly ethane and $C_3^+$ hydrocarbons, (d) carrying out oxidative coupling of methane (OCM) in an OCM zone to produce a first effluent containing mainly ethylene, and a second effluent containing mainly hydrogen, carbon monoxide and carbon dioxide, (e) dimerising a major portion of the first effluent obtained from step (d) in a dimerisation zone to produce an effluent containing mainly n-butene, (f) isomerising a major portion of the effluent obtained from step (e) in an isomerisation zone to produce an effluent containing mainly isobutene, (g) synthesizing at least one alcohol in an alcohol synthesis zone, from a portion of the fourth fraction obtained from step (c) and a portion of the first fraction obtained from step (c), said portions being compressed before their introduction into the alcohol synthesis zone to form an effluent containing at least one alcohol, (h) combining a major portion of the effluent obtained in step (f) with at least a portion of the effluent obtained in step (g) to synthesize at least one alkyl tertiobutyl ether in an alkyl tertiobutyl ether synthesis zone.

2. Process according to claim 1 wherein, prior to prereforming, said feedstock is separated into a first fraction containing mainly methane which constitutes the actual feedstock for step (a), and a second fraction containing mainly hydrocarbons containing at least two carbon atoms per molecule.

3. Process according to claim 2, wherein said separation is carried out in the separation zone described in step (c).

4. Process according to claim 1 wherein the supply to the OCM zone is constituted by at least a portion of the second fraction described in step (c).

5. Process according to claim 1 wherein the OCM zone is constituted by the section of the oxypyrolysis zone in which the OCM is carried out.

6. Process according to claim 5 wherein the section of the oxypyrolysis zone in which pyrolysis is carried out is supplied by the fifth fraction described in step (c).

7. Process according to claim 1 wherein a compressed portion of the second effluent obtained from step (d) is introduced into the alcohol synthesis zone.

8. A process according to claim 1 for the synthesis of methyl tertiobutyl ether.

9. A process according to claim 1 for the synthesis of ethyl tertiobutyl ether.

10. A process for the simultaneous production of at least one alkyl tertiobutyl ether and a liquid fuel from natural gas, said process comprising the following steps:

(1) a major portion of the second effluent from the OCM zone described in step (2) is dried and compressed then sent to a separation zone to produce the following effluents:
    a first fraction containing mainly carbon dioxide,
    a second fraction containing mainly methane,
    a third fraction containing mainly ethylene,
    a fourth fraction containing mainly hydrogen and carbon monoxide,
    a fifth fraction containing mainly ethane and $C_3^+$ hydrocarbons, (2) oxidative coupling of methane is carried out in an OCM zone to produce a first effluent containing mainly ethylene and a second effluent containing mainly hydrogen, carbon monoxide and carbon dioxide, (3) a portion of the first effluent obtained from step (2) is dimerised in a dimerisation zone to produce an effluent containing mainly n-butene, (4) a major portion of the effluent obtained from step (3) is isomerised in an isomerisation zone to produce an effluent containing mainly isobutene, (5) synthesis of at least one alcohol is carried out in an alcohol synthesis zone using a portion of the fourth fraction obtained from step (1) and a portion of the first fraction obtained from step (1), said portions being compressed before introduction into the alcohol synthesis zone to form an effluent containing mainly at least one alcohol, (6) a further portion of the first effluent obtained from step (2) undergoes at least one of the following reactions: dimerisation or oligomerisation in a reaction zone, to produce an effluent containing mainly liquid fuel, (7) a major portion of the effluent obtained from step (4) is combined with at least a portion of the effluent obtained from step (5) to synthesize at least one alkyl tertiobutyl ether in an alkyl tertiobutyl ether synthesis zone, (8) a major portion of the effluent obtained from step (6) is mixed with a portion of the alkyl tertiobutyl ether(s) to produce a liquid fuel base.

* * * * *